United States Patent [19]

Welch et al.

[11] Patent Number: 4,779,290
[45] Date of Patent: Oct. 25, 1988

[54] CUT RESISTANT SURGICAL GLOVES

[75] Inventors: Robert A. Welch, Plymouth; Mitchell P. Dombrowski, Grosse Point Farms, both of Mich.

[73] Assignee: Wayne State University, Detroit, Mich.

[21] Appl. No.: 23,831

[22] Filed: Mar. 9, 1987

[51] Int. Cl.$^4$ .............................................. A41D 19/00
[52] U.S. Cl. ....................................... 2/161 R; 2/167
[58] Field of Search ............... 2/161 R, 159, 164, 167, 2/168, 169

[56] References Cited

U.S. PATENT DOCUMENTS

| | | | |
|---|---|---|---|
| 1,157,646 | 10/1915 | Miller | 2/168 |
| 2,373,940 | 4/1945 | Beall | 2/168 |
| 2,747,229 | 5/1956 | Teague | 2/167 X |
| 2,864,091 | 12/1958 | Schneider | 2/161 R |
| 3,934,062 | 1/1976 | Tillotsen et al. | 2/167 X |
| 4,218,779 | 8/1980 | Hart et al. | 2/168 |
| 4,283,244 | 8/1981 | Hashimi | 2/168 X |
| 4,526,828 | 7/1985 | Fogt et al. | 2/161 R X |

Primary Examiner—Louis K. Rimrodt
Assistant Examiner—Judith L. Olds
Attorney, Agent, or Firm—Reising, Ethington, Barnard, Perry & Milton

[57] ABSTRACT

A surgical glove (10) includes a ventral side (12) and a dorsal side (14) integrally connected thereto. The sides (12,14) include a thin layer (16) of stretchable air and water impermeable material and the dorsal side (14) includes a layer (18) of flexible armor (18) embedded in the stretchable air and water impermeable material (16). A method of making the surgical glove (10) includes the steps of dipping a mold shell (24) having the configuration of a human hand with a ventral side and a dorsal side (30) into a liquid (34) which is curable to the stretchable air and water impermeable material (16). A hand shaped layer (18) of the flexible armor is disposed on the dorsal side (30) of the shell (24) prior to curing the liquid (34). The shell (24) is dipped into the liquid (34) a second time to embed the fiber (18) within the liquid (34). Finally, the liquid (34) is cured to the stretchable air and water impermeable material (16).

9 Claims, 1 Drawing Sheet

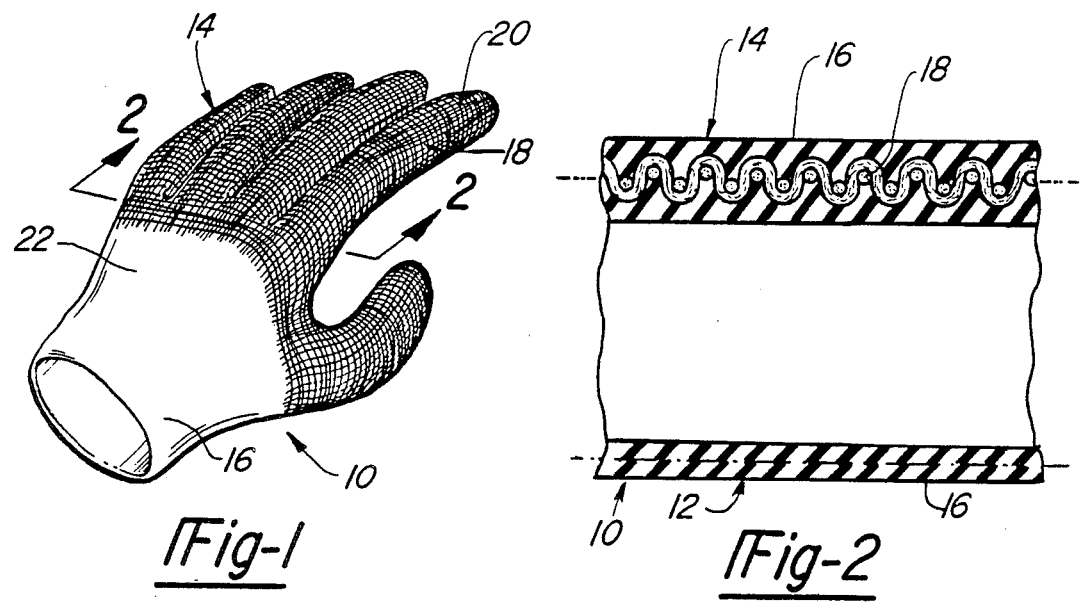
Fig-1
Fig-2
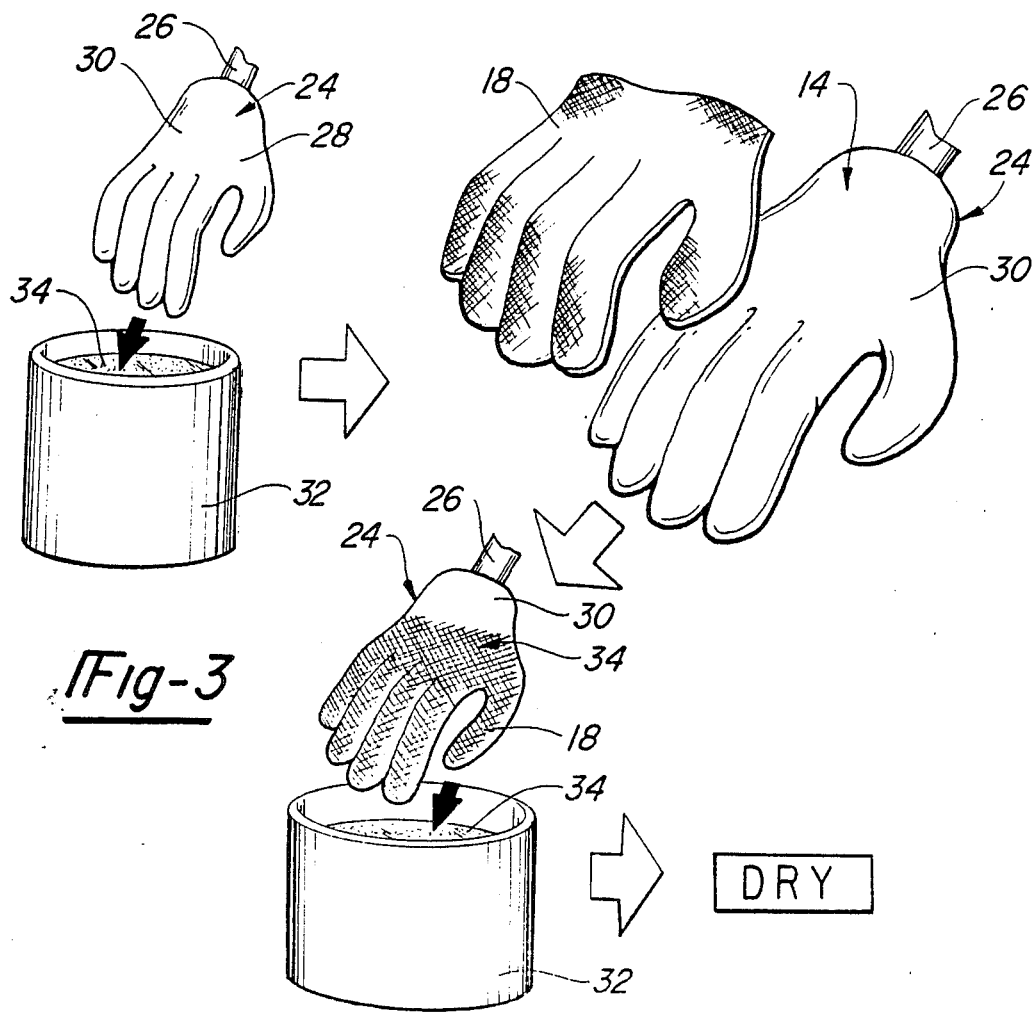
Fig-3
DRY

CUT RESISTANT SURGICAL GLOVES

TECHNICAL FIELD

The instant invention relates to highly stretchable gloves particularly well suited for use as surgical gloves. More particularly, the invention provides a protective glove incorporating a cut resistant fiber.

BACKGROUND ART

There is a need in surgical situations for a cut resistant surgical glove. Such a glove can contribute to the prevention of transmission of blood borne infections, such as AIDS and hepatitis during surgery. For example, it is common during surgery for a surgeon to be nicked by a scalpel. In this manner, the scalpel can transmit blood borne infections from the patient to the surgeon.

Presently, surgical gloves are made from a thin layer of latex. Examples of latex rubber gloves for medical use are disclosed in the U.S. Pats. Nos. 4,115,873 to Stansbury, issued Sept. 26, 1978; 4,189,787 to Stansbury, issued Feb. 26, 1980; and 4,218,778 to Stansbury, issued Aug. 26, 1980. This type of latex glove provides excellent tactility for the surgeon yet is easily susceptible to scalpel cuts.

Cut resistant gloves known in the prior art include various means incorporated therein for guarding against injury by a knife or a scalpel. For example, the U.S. Pat. No. 4,507,804 to Consigny, issued Apr. 2, 1985, discloses a finger guard for protection against injury by a knife. The finger guard consists of a multiplicity of spaced apart inner connected metallic lamellae. The U.S. Pat. No. 3,184,756 to De Luca, Jr., issued May 25, 1965, provides a protective glove incorporating armor pieces in the finger portions. The U.S. Pat. No. 4,470,251 to Bettcher, issued Sept. 11, 1984, discloses a knitted safety glove made of yarn having a core of two longitudinal strands of annealed stainless steel wire and one strand of high strength aramid fiber surrounded by an aramid fiber wrapped thereabout in one direction and a layer of nylon wrapped upon the first layer and in the opposite direction.

These prior art gloves and finger guards are inapplicable to the situation confronted by the surgeon wherein it is first necessary to have sufficient tactility to perform delicate surgical maneuvers while it is desirable to have protection against scalpel cuts. The aforementioned prior art patents disclose either gloves which provide tactility but no cut protection or provide knife cut protection with the sacrifice of the necessary tactility.

There exists various methods for manufacturing multi-layered gloves having protective layers. The U.S. Pat. No. 3,945,049 to Barlow, issued Mar. 23, 1976 discloses a process for the manufacture of gloves including the steps of precoating the fabric, curing the precoat, and then welding two pieces together along a weld zone thereby creating a seam. The U.S. Pat. No. 4,371,988 to Berend, issued Feb. 8, 1983, discloses a method for making a protective two layer coating on a glove including the steps of soaking a mold covered with a lining in a first mixture of a resin and pregelling the first protective layer. The lining provided with the first layer is then subjected to a partial soaking in a second mixture of resin and the layers are gelled.

The U.S. Pat. No. 4,578,826 to Adiletta, issued Apr. 1, 1986, discloses a process for manufacturing protective gloves including the steps of drawing a vacuum to the interior of a fabric shell to cause a binding agent and fibers from a slurry to be deposited on the outer surface of the shell. A composite structure is cured to set the matrix in the desired shape.

The U.S. Pat. No. 4,218,779 to Hart et al, issued Aug. 26, 1980, discloses a method of manufacturing a chemical resistant glove including several steps of dipping treated substrates in a bath containing a latex dispersion. Latex dipped gloves are air or oven dried to produce a rubber coated former.

The present invention provides a surgical glove allowing the surgeon to have the tactile response necessary for delicate surgical maneuvers but also provides a cut resistant surface. The present invention further provides a method for manufacturing the glove.

SUMMARY OF THE INVENTION

In accordance with the present invention, there is provided a surgical glove including a ventral side and a dorsal side integrally connected to the ventral side. Both sides include a thin layer of stretchable air and water impermeable material and the dorsal side includes a layer of flexible armor material embedded in the stretchable air and water impermeable material.

The invention further provides a method of making the surgical glove including the steps of dipping the mold shell having the configuration of a human hand with a ventral side and a dorsal side into a liquid which is curable to a stretchable air and water impermeable material. A hand shaped layer of the flexible armor material is disposed on the dorsal side of the shell prior to curing the liquid. The shell is then dipped into the liquid a second time to embed the armor material with the liquid. The liquid is finally cured to the stretchable air and water impermeable material having the armor material embedded within the dorsal side.

FIGURES IN THE DRAWINGS

Other advantages of the present invention will be readily appreciated as the same becomes better understood by reference to the following detailed description when considered in connection with the accompanying drawings wherein:

FIG. 1 is a perspective view of a surgical glove constructed in accordance with the present invention;

FIG. 2 is fragmentary cross sectional view taken substantially along lines 2—2 of FIG. 1; and FIG. 3 is schematic perspective view showing the subject method for manufacturing the surgical glove.

DETAILED DESCRIPTION OF THE DRAWINGS

A surgical glove constructed in accordance with the present invention is generally shown at 10 in FIGS. 1 and 2 of the drawings.

The glove 10 includes a ventral side generally indicated at 12 and dorsal side generally indicated at 14 integrally connected together. By being integral, there is no seam between the ventral side 12 and dorsal side 14. The sides 12,14 include a thin layer 16 of a stretchable air and water impermeable material and the dorsal side 14 includes a layer 18 of flexible armor material embedded in the flexible material 16. The armor material 18 is a cut resistant fiber impregnated with the stretchable air and water impermeable material 16 as shown in FIG. 2, the layer of impermeable material 16 is disposed throughout the interstices of the fibers 18.

The invention thereby provides a cut resistant surface on the dorsal side or aspect of the glove protecting the surgeon from cuts on the side of the hand which is most susceptible to exposure to the scalpel blade. The fiber retains the impermeability of the dorsal side 14 in the sharp tool environment. The glove further provides a thin tactilely responsive layer 16 on the ventral side 12 of the glove 10 which gives the surgeon the tactile sensitivity necessary for delicate surgical maneuvers.

The glove 10 is seamless, seams being undesirable in a surgical glove as there exists a decreased tactility about the extended area of the seam. Since the flexible cut resistant fiber is impregnated with the stretchable, air and water impermeable material 16, the entire glove can be sterilized and provide a sterile environment covering the surgeon's hands. To provide comfort during flexing of the hand which stretches the dorsal aspect of the glove, the cut resistant fiber layer is flexible.

More specifically, the fiber 18 is a stretchable interwoven material which can be made from a synthetic fiber. Examples of fibers which are cut resistant are nylon and the aramid fibers. Aramid fibers are particularly well suited for the present invention as they are heat resistant and therefore can be easily sterilized, they are dimensionally stable, and have ultra high strength and high modulus. A particular aramid fiber well suited for the present invention is the ultra high strength, high modulus fiber Kevlar ®, manufactured by E.I. DuPont.

The flexible air and water impermeable material is a film forming liquid, such as latex or other synthetic material. For example, natural latex, such as Lotol 185 ®, can be used. Latexes of other elastomeric material such as polyacrylates e.g. polyethyl acrylate, polybutadiene, styrene-butadiene copolymer, acrylonitrile-butadiene rubber and neoprene (polychloroprene) can be employed for this purpose.

It is not essential that the dorsal side of the glove 10 be completely covered by the woven fabric 18. As shown in FIG. 1, the dorsal side 14 of the glove 10 includes finger portions 20 and a backhand portion 22. The fiber 18 impregnated with the impermeable material 16 extends over the finger portions 20 and partially over the backhand portion 16. As shown in FIG. 1, the wrist portion does not include the fiber 18. Alternatively, of course, the fiber 18 may extend completely over the dorsal side 14 of the glove 10.

The method of making the surgical glove 10 in accordance with the present invention is illustrated in FIG. 3. A mold shell generally indicated at 24 includes a handle portion 26 and a hand-form portion 28. The hand-form portion 28 includes a ventral side (not shown in the Figures) and a dorsal side 30. The hand-form portion 28 is dipped into a container 32 of liquid 34, the liquid 34 being curable to the stretchable, air and water impermeable material 16 as discussed above. A hand shaped layer 18 of the flexible cut resistant fiber is disposed on the dorsal side 30 of the shell 24 prior to complete curing of the liquid 34 which coats the shell 24. The liquid 34 is of a viscosity so that the fiber 18 substantially adheres to the layer of liquid 34 on the shell 24. The liquid can be of a low viscosity so as to form a thin layer. The liquid can be partially cured prior to application of the fiber.

The shell 24 is dipped into the container 32 of liquid 34 a second time to impregnate and cover the fiber 18 with the liquid 34. Alternatively, a second container of either the same liquid or different liquid may be utilized for the second dipping step.

The shell 24 including the liquid impregnated fiber 18 on the dorsal side 30 and the purely liquid layer on the ventral side is either air dried or subjected to heat to cure the liquid to the stretchable, air and water impermeable material 16.

The subject method thereby provides a seamless surgical glove constructed of a stretchable air and water impermeable material with a stretchable woven armor of cut resistant fiber on the dorsal side.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A surgical glove (10) comprising: a ventral side (12) and a dorsal side (14) integrally connected to said ventral side (12), said sides (12,14) including a thin layer (16) of stretchable air and water impermeable material, and characterized by said dorsal side (14) including a layer (18) of flexible armor material embedded in said stretchable, air and water impermeable material (16) for preventing cutting through said material (16) to retain the impermeability of said dorsal side (14) in a sharp tool environment and said ventral side comprising a thin tactilely sensitive layer providing the combination of cut protection with tactile sensitivity for surgical maneuvers.

2. A glove as set forth in claim 1 further characterized by said armor material comprising interwoven fibers (18).

3. A glove as set forth in claim 2 further characterized by said interwoven fibers defining intensities therebetween, said thin layer of said impermeable material being disposed throughout the interstices of said fibers (18).

4. A glove as set forth in claim 3 further characterized by said fibers interwoven into a stretchable cloth.

5. A glove as set forth in claim 4 further characterized by said fibers (18) being a synthetic fiber.

6. A glove as set forth in claim 5 further characterized by said fibers (18) being nylon.

7. A glove as set forth in claim 5 further characterized by said fibers (18) being an aramid fiber.

8. A glove as set forth in claim 1 further characterized by said impermeable material (16) being latex.

9. A glove as set forth in claim 1 further characterized by said dorsal side (14) of said glove (10) including finger portions (20) and a backhand portion (22), said armor material including fibers (18) extending over said finger portions (20) and partially over said backhand portion (16).

* * * * *